United States Patent

Mayer et al.

Patent Number: 5,160,365
Date of Patent: Nov. 3, 1992

[54] HERBICIDAL 1,3,5-TRIAZIN-2-YLUREIDOSULFONYL-BENZOIC ESTERS

[75] Inventors: Horst Mayer, Ludwigshafen; Gerhard Hamprecht, Weinheim; Karl-Otto Westphalen, Speyer; Helmut Walter, Obrigheim; Matthias Gerber, Mutterstadt, all of Fed. Rep. of Germany

[73] Assignee: BASF Aktiengesellschaft, Ludwigshafen, Fed. Rep. of Germany

[21] Appl. No.: 758,552

[22] Filed: Sep. 12, 1991

[30] Foreign Application Priority Data

Sep. 18, 1990 [DE] Fed. Rep. of Germany ....... 4029484

[51] Int. Cl.$^5$ .................... C07D 251/42; A01N 43/66
[52] U.S. Cl. ........................................ 71/93; 544/211
[58] Field of Search .................... 71/93; 544/211

[56] References Cited

U.S. PATENT DOCUMENTS

| | | | |
|---|---|---|---|
| 4,238,621 | 12/1980 | Levitt | 560/12 |
| 4,383,113 | 5/1983 | Levitt | 544/211 |
| 5,071,470 | 12/1991 | Mayer et al. | 71/93 |

FOREIGN PATENT DOCUMENTS

| | | |
|---|---|---|
| 79805/82 | 5/1982 | Australia . |
| 162723 | 11/1985 | European Pat. Off. . |
| 382437 | 8/1990 | European Pat. Off. . |
| 388873 | 9/1990 | European Pat. Off. . |
| 89/02595 | 3/1989 | World Int. Prop. O. . |
| 89/09214 | 10/1989 | World Int. Prop. O. . |

OTHER PUBLICATIONS

Chemical Abstracts, vol. 107, No. 19, 9. Nov. 1987, Columbus, Ohio USA Du Pont De Nemours; E. L. and Co. "Preparation of 2-(((2-pyrimidinyl and 1,3,5-triazin-2-yl)ureido) sulfonyl) benzoates as herbicides and plant growth regulators." p. 729, colum 1, abstract No. 176 061n of JPpn. Kokai Tokkyo Koho JP 62,129,276.

*Primary Examiner*—John M. Ford
*Attorney, Agent, or Firm*—Oblon, Spivak, McClelland, Maier & Neustadt

[57] ABSTRACT

1,3,5-Triazin-2-ylureidosulfonylbenzoic esters of the formula I

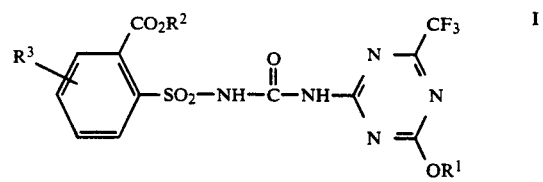

where $R^1$ is methyl or ethyl, $R^2$ is n-propyl, i-propyl, 2-haloethyl or 2-methoxyethyl, and, when $R^3$ is methyl or methoxy, is methyl or ethyl, $R^3$ is hydrogen, fluorine, chlorine, methyl or methoxy, and the salts thereof which can be used in agriculture, are prepared and used as described.

8 Claims, No Drawings

HERBICIDAL 1,3,5-TRIAZIN-2-YLUREIDOSULFONYLBENZOIC ESTERS

The present invention relates to 1,3,5-triazin-2-ylureidosulfonylbenzoic esters of the formula I

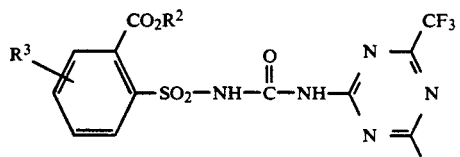

where
R[1] is methyl or ethyl;
R[2] is n-propyl, i-propyl, 2-haloethyl or 2-methoxyethyl and, when R[3] is methyl or methoxy, is methyl or ethyl;
R[3] is hydrogen, fluorine, chlorine, methyl or methoxy, and the salts thereof which can be used in agriculture.

The present invention also relates to a process for preparing the compounds I and the use thereof as herbicidal agents.

EP-A 7687, EP-A 30 138 and EP-A 57 546 relate to sulfonylureas which have a herbicidal action and whose formula embraces the compounds I defined above.

Whereas the closest structures described in EP-A 57 546 are only 1,3,5-triazine N-oxide derivatives I′ where, inter alia,
X and Y are each, independently of one another, methyl or methoxy and
O is oxygen in position 1, 3 or 5 of the triazinyl ring, the emphasis in EP-A 30 138 is on alterations in the carboxylate ortho to the sulfonylamino group. Haloalkyl substituents for the triazine moiety are not described therein.

Only EP-A 7687 describes a triazinyl derivative with a haloalkyl radical (I″).

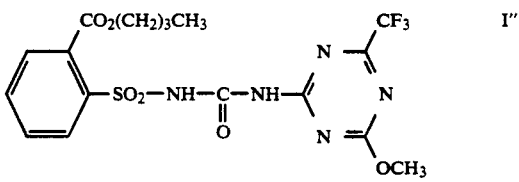

U.S. Pat. No. 5,071,470 describes 1,3,5-triazin-2-ylureidosulfonylbenzoic esters of the formula I where R[2] is methyl or ethyl and R[3] is hydrogen, fluorine or chlorine.

It is an object of the present invention to synthesize sulfonylureas whose properties are better than those of known representatives of this class of herbicides.

We have found that this object is achieved by the 1,3,5-triazin-2-ylureidosulfonylbenzoic esters of the formula I defined above.

The novel sulfonylureas of the formula I can be obtained in a variety of ways which are described in the literature. Particularly advantageous routes (A–C) are described in detail hereinafter by way of example.

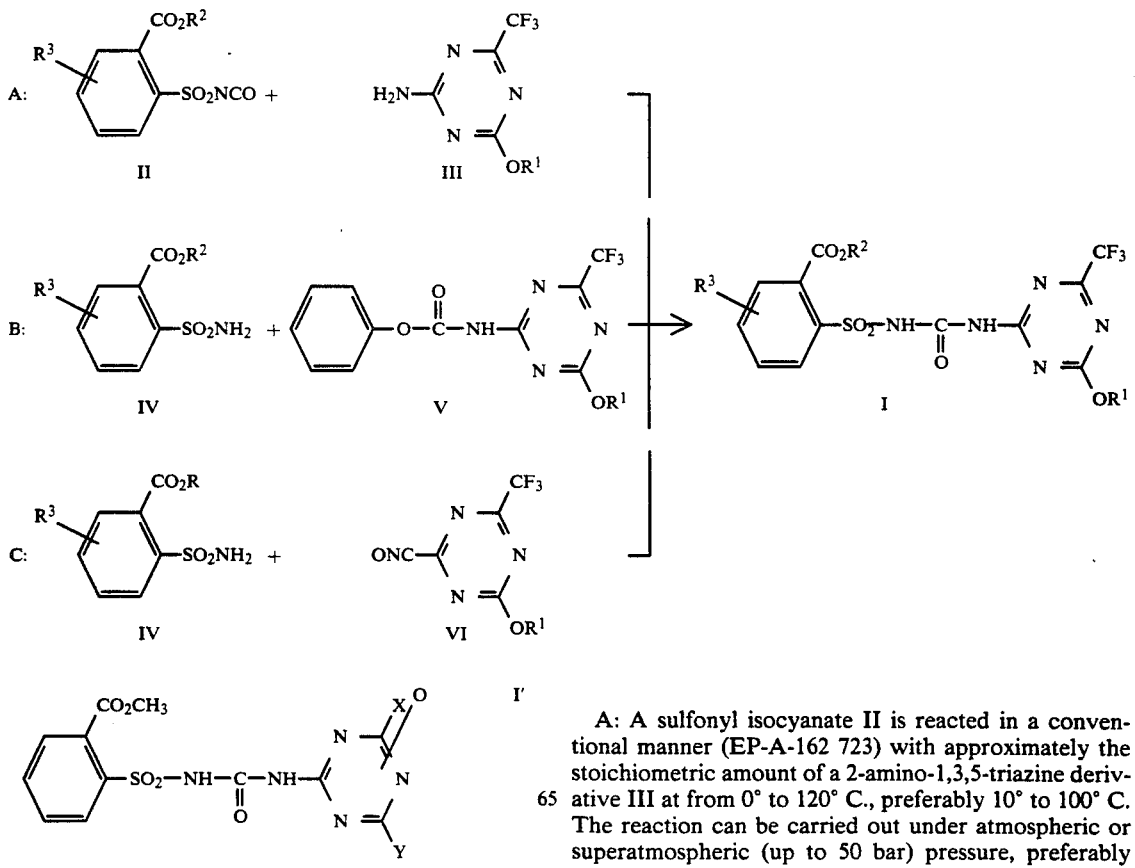

A: A sulfonyl isocyanate II is reacted in a conventional manner (EP-A-162 723) with approximately the stoichiometric amount of a 2-amino-1,3,5-triazine derivative III at from 0° to 120° C., preferably 10° to 100° C. The reaction can be carried out under atmospheric or superatmospheric (up to 50 bar) pressure, preferably under from 1 to 5 bar, continuously or batchwise.

It is expedient to use for these reactions solvents and diluents which are inert under the reaction conditions. Examples of suitable solvents are halohydrocarbons, especially chlorohydrocarbons, eg. tetrachloroethylene, 1,1,2,2- or 1,1,1,2-tetra-chloroethane, dichloropropane, methylene chloride, dichlorobutane, chloroform, chloronaphthalene, dichloronaphthalene, tetrachloromethane, 1,1,1- or 1,1,2-trichloroethane, trichloroethylene, pentachloroethane, o-, m-, p-difluorobenzene, 1,2-dichloroethane, 1,1-dichloroethane, 1,2-cis-dichloroethylene, chlorobenzene, fluorobenzene, bromobenzene, iodobenzene, o-, m-, p-dichlorobenzene, o-, m-, p-dibromobenzene, o-, m-, p-chlorotoluene, 1,2,4-trichlorobenzene; ethers, eg. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole, $\beta,\beta'$-dichlorodiethyl ether; nitrohydrocarbons such as nitromethane, nitroethane, nitrobenzene, o-, m-, p-chloronitrobenzene, o-nitrotoluene; nitriles such as acetonitrile, butyronitrile, isobutyronitrile, benzonitrile, m-chlorobenzonitrile; aliphatic or cycloaliphatic hydrocarbons, eg. heptane, pinane, nonane, o-, m-, p-cymene, petroleum fractions boiling within the range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane, octane; esters, eg. ethyl acetate, ethyl acetoacetate, isobutyl acetate; amides, eg. formamide, methylformamide, dimethylformamide; ketones, eg. acetone, methyl ethyl ketone and mixtures thereof. The solvent is expediently used in an amount of from 100 to 2000%, preferably from 200 to 700%, of the weight of starting material II.

The compound II required for the reaction is generally employed in an amount which is approximately equimolar (±0–20%, for example) to that of the starting material III. The starting material III can be introduced into one of the abovementioned diluents and then starting material II can be added.

However, it is expedient to carry out the process for preparing the novel compounds in such a way that starting material II is introduced, where appropriate into one of the abovementioned diluents, and then starting material III is added.

To complete the reaction, the mixed components are then stirred at from 0° to 120° C., preferably 10° to 100° C., in particular 20° to 80° C., for from 20 minutes to 24 hours.

The reaction rate can be increased advantageously by adding a tertiary amine, eg. pyridine, $\alpha$-, $\beta$- or $\gamma$-picoline, 2,4- or 2,6-lutidine, 2,4,6-collidine, p-dimethylaminopyridine, trimethylamine, triethylamine, tri(n-propyl)amine, 1,4-diazabicyclo[2.2.2]octane (DABCO) or 1,8-diazabicyclo[5.4.0]undec-7-ene in an amount of from 0.01 to 1 mole per mole of starting material II.

The product I is isolated from the reaction mixture in a conventional manner, eg. after removal of solvent by distillation or directly by filtration with suction. The residue can then be washed with water or dilute acid to remove basic impurities. However, the residue can also be dissolved in a water-immiscible solvent and washed as described. The required products are obtained in pure form in this way but, if necessary, they can be purified by recrystallization, stirring in an organic solvent which dissolves the impurities, or chromatography.

This reaction is preferably carried out in acetonitrile, methyl tert-butyl ether, toluene or methylene chloride in the presence of from 0 to 100 mole equivalents, preferably 0 to 50 mole equivalents, or a tertiary amine such as 1,4-diazabicyclo[2.2.2]octane or triethylamine.

B: A sulfonamide of the formula IV is reacted in a conventional manner (EP-A-141 777 and EP-A-101 670) in an inert organic solvent with approximately the stoichiometric amount of a phenyl carbamate V at from 0° to 120° C., preferably 20° to 100° C. The reaction can be carried out under atmospheric or superatmospheric (up to 50 bar) pressure, preferably under from 1 to 5 bar, continuously or batchwise.

It is possible in this case to add bases such as tertiary amines which increase the reaction rate and improve the product quality. Bases suitable for this are those indicated under A, especially triethylamine, 2,4,6-collidine, 1,4-diazabicyclo[2.2.2]octane (DABCO) or 1,8-diazabicyclo[5.4.0]undec-7-ene (DBU) in an amount of from 0.01 to 1 mole per mole of starting material IV.

It is expedient to use as solvent or diluent one of those indicated under A.

The solvent is used in an amount of from 100 to 2000%, preferably from 200 to 700%, of the weight of precursor IV.

The compound IV required for the reaction is generally employed in an amount which is approximately equimolar (±0–20%, for example) to that of the starting material V. The starting material V can be introduced into one of the abovementioned diluents and then starting material IV can be added.

However, it is also possible to introduce starting material IV into one of the said solvents and then to add the carbamate V. In both cases, one of the said bases can be added as catalyst before or during the reaction.

To complete the reaction, the mixed components are stirred at from 0° to 120° C., preferably 10° to 100° C., in particular 20° to 80° C., for from 20 minutes to 24 hours.

The sulfonylureas of the formula I are isolated from the reaction mixture by conventional methods as described under A.

C: A sulfonamide of the formula IV is reacted in a conventional manner (EP-A-234 352) in an inert organic solvent with approximately the stoichiometric amount of an isocyanate VI at from 0° to 150° C., preferably 10° to 100° C. The reaction can be carried out under atmospheric or superatmospheric (up to 50 bar) pressure, preferably under from 1 to 5 bar, continuously or batchwise.

It is possible to add bases such as tertiary amines before or during this reaction to increase its rate and improve the product quality. Bases suitable for this are those indicated under A, especially triethylamine or 2,4,6-collidine, in an amount of from 0.01 to 1 mole per mole of starting material IV.

It is expedient to use as solvent one of those indicated under A. The solvent is used in an amount of from 100 to 2000%, preferably from 200 to 700%, of the weight of precursor IV.

The compound IV required for the reaction is generally employed in an amount which is approximately equimolar (±0–20%, for example) to that of precursor VI. The starting material VI can be introduced into one of the said diluents and then the starting material IV can be added.

However, it is also possible to introduce the sulfonamide first and then to add the isocyanate VI.

To complete the reaction, the mixed components are stirred at from 0° to 120° C., preferably 10° to 100° C., in particular 20° to 80° C., for from 20 minutes to 24 hours.

The product I can be obtained from the reaction mixture in a conventional manner as described under A.

The sulfonyl isocyanates of the formula II used as precursors were obtained by methods identical or similar to those described in the literature (eg. EP-A-7687).

Carbamates of the formula V can be obtained by reactions identical or similar to those disclosed in, for example, EP-A-141 777, but they can also be prepared from the corresponding isocyanates of the formula VI by reaction with phenol.

The salts of the compounds I can be obtained in a conventional manner (EP-A-304 282, U.S. Pat. No. 4,599,412). They are obtained by deprotonation of the appropriate sulfonylureas I in water or an inert organic solvent at from −80° C. to 120° C., preferably 0° C. to 60° C. in the presence of a base.

Examples of suitable bases are alkali metal or alkaline earth metal hydroxides, hydrides, oxides or alcoholates such as sodium, potassium and lithium hydroxide, sodium methanolate, ethanolate and tert-butanolate, sodium and calcium hydride and calcium oxide.

Besides water, examples of suitable solvents are alcohols such as methanol, ethanol and tert-butanol, ethers such as tetrahydrofuran and dioxane, acetonitrile, dimethylformamide, ketones such as acetone and methyl ethyl ketone and halohydrocarbons.

The deprotonation can be carried out under atmospheric pressure or up to 50 bar, preferably under atmospheric pressure or up to 5 bar.

The sulfonamides required as starting materials of the formula IV can be prepared from the corresponding anthranilic esters by the Meerwein reaction and subsequent reaction with ammonia (Houben-Weyl, 9, 557f (1955)).

The 2-amino-4-methoxy-6-trifluoromethyl-1,3, 5-triazine and 2-amino-4-methoxy-6-trifluoromethyl-1,3, 5-triazine precursors are disclosed in Yakugaku Zasshi 95 (1975) 499.

The compounds I and the herbicidal agents containing them, and their environmentally compatible salts of alkali metals and alkaline earth metals, can control weeds in crops such as wheat very efficiently without damaging the crop plants, and this effect occurs especially at low application rates.

They can be applied, for example, in the form of directly sprayable solutions, powders, suspensions, including high-percentage aqueous, oily or other suspensions or dispersions, emulsions, oil dispersions, pastes, dusting or broadcasting agents or granules by spraying, atomizing, dusting, broadcasting or watering. The application forms depend on the purposes for which they are used; they ought in every case to ensure the finest possible distribution of the active ingredients according to the invention.

The compounds I are generally suitable for preparing directly sprayable solutions, emulsions, pastes or oil dispersions. Suitable inert additives are mineral oil fractions of moderate to high boiling point such as kerosene or diesel oil, also coaltar oils and oils of vegetable or animal origin, aliphatic, cylic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or highly polar solvents such as N,N-dimethylformamide, dimethyl suloxide, N-methylpyrrolidone or water.

Aqueous application forms can be prepared from emulsion concentrates, dispersions, pastes, wettable powders or water-dispersible granules by adding water. To prepare emulsions, pastes or oil dispersions, the substances can be homogenized, as such or dissolved in an oil or solvent, using wetting agents, adhesion promoters, dispersants or emulsifiers, in water. However, it is also possible to prepare concentrates which are composed of active substance, wetting agent, adhesion promoter, dispersant or emulsifier and, where appropriate, solvent or oil and which are suitable for dilution with water.

Suitable surfactants are the alkali metal, alkaline earth metal and ammonium salts of aromatic sulfonic acids, eg. lignin-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, and of fatty alcohol glycol ethers, products of the condensation of sulfonated naphthalene and its derivatives with formaldehyde, products of the condensation of naphthalene or naphthalenesulfonic acids with phenol and formaldehyde, polyoxyethylene octylphenol ether, ethoxylated isooctyl-, octyl- or nonylphenol, alkylphenol and tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders and dusting and broadcasting agents can be prepared by mixing or grinding the active substances together with a solid carrier.

Granules, eg. coated, impregnated or homogeneous granules, can be prepared by binding the active ingredients to solid carriers. Examples of solid carriers are mineral earths such as silica gel, silicic acids, silicates, talc, kaolin, limestone, lime, chalk, bole, loess, clay, dolomite, diatomaceous earth, calcium and magnesium sulfates, magnesium oxide, ground plastics, fertilizers such as ammonium sulfate, ammonium phosphate, ammonium nitrate, ureas and vegetable products such as cereals flour, bark meal, wood meal and nutshell meal, cellulose powders or other solid carriers.

The formulations generally contain from 0.1 to 95% by weight, preferably from 0.5 to 90% by weight, of active ingredient.

Examples of formulations are as follows:

I. a solution of 90 parts by weight of compound No. 1 and 10 parts by weight of N-methyl-$\alpha$-pyrrolidone is suitable for use in the form of very small drops;

II. 20 parts by weight of compound No. 1 are dissolved in a mixture composed of 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil. A fine dispersion of this solution in 100,000 parts by weight of water contains 0.02% by weight of active ingredient;

III. 20 parts by weight of compound No. 1 are dissolved in a mixture composed of 40 parts by weight of cyclohexanone, 30 parts by weight of isobutanol, 20 parts by weight of the adduct of 7 moles of ethylene oxide and 1 mole of isooctylphenol and 10 parts by weight of the adduct of 40 moles of ethylene oxide and 1 mole of castor oil. A fine dispersion of this solution in 100,000 parts by weight of water contains 0.02% by weight of the active ingredient;

IV. 20 parts by weight of compound No. 1 are dissolved in a mixture composed of 25 parts by weight of cyclohexanone, 65 parts by weight of a mineral oil fraction of boiling point 210° to 280° C. and 10 parts by weight of the adduct of 40 moles of ethylene oxide and 1 mole of castor oil. A fine dispersion of this solution in 100,000 parts by weight of water contains 0.02% of the active ingredient;

V. 20 parts by weight of compound No. 1 are mixed thoroughly and ground in a hammer mill with 3 parts by weight of sodium diisobutylnaphthalene-α-sulfonate, 17 parts by weight of the sodium salt of a ligninsulfonic acid from a sulfite waste liquor and 60 parts by weight of powdered silica gel. A fine dispersion of this mixture in 20,000 parts by weight of water contains 0.1% by weight of the active ingredient and can be used for spraying;

VI. 3 parts by weight of active ingredient No. 1 are mixed with 97 parts by weight of finely divided kaolin. This dusting agent contains 3% by weight of the active ingredient;

VII. 30 parts by weight of active ingredient No. 1 are intimately mixed with 92 parts by weight of powdered silica gel and 8 parts by weight of liquid paraffin which was sprayed onto the surface of this silica gel. This formulation confers good adhesion on the active ingredient;

VIII. 20 parts by weight of active ingredient No. 1 are intimately mixed with 2 parts by weight of calcium dodecylbenzenesulfonic acid, 8 parts by weight of fatty alcohol polyglycol ether, 2 parts by weight of the sodium salt of a phenol/urea/formaldehyde condensate and 68 parts by weight of a liquid paraffin. A stable oily dispersion is obtained.

Application is possible by a pre-emergence or post-emergence process. If the active ingredients are less well tolerated by certain crop plants, it is possible to use application techniques in which the herbicidal agents are sprayed in such a way that the leaves of the sensitive crop plants are touched as little as possible while the active ingredients reach the leaves of unwanted plants underneath or the bare soil (post-directed, lay-by).

The application rates for the active ingredient depend on the aim of the control, the season, the target plants and the stage of growth and are from 0.001 to 3.0, preferably 0.01 to 2.0 kg/ha.

In view of the wide variety of application methods, the novel compounds or the agents containing them can also be employed in a number of other crop plants for removing unwanted plants. Examples of suitable crops are the following:

| Botanical name | English name |
|---|---|
| Allium cepa | cooking onion |
| Ananas comosus | pineapple |
| Arachis hypogaea | peanut |
| Asparagus officinalis | asparagus |
| Beta vulgaris spp. altissima | sugar beet |
| Beta vulgaris spp. rapa | fodder beet |
| Brassica napus var. napus | rape |
| Brassica napus var. napobrassica | Swedish turnip |
| Brassica rapa var. silvestris | turnip rape |
| Camellia sinensis | tea plant |
| Carthamus tinctorius | safflower |
| Carya illinoinensis | pecan nut |
| Citrus limon | lemon |
| Citrus sinensis | orange |
| Coffea arabica (Coffea canephora, Coffea liberica) | coffee |
| Cucumis sativus | cucumber |
| Cynodon dactylon | Bermuda grass |
| Daucus carota | carrot |
| Elaeis guineensis | oil palm |
| Fragaria vesca | strawberry |
| Glycine max | soybean |
| Gossypium hirsutum (Gossypium arboreum, Gossypium herbaceum, Gossypium vitifolium) | cotton |
| Helianthus annuus | sunflower |
| Hevea brasiliensis | para rubber tree |
| Hordeum vulgare | barley |
| Humulus lupulus | hops |
| Ipomoea batatas | sweet potatoes |
| Juglans regia | walnut |
| Lens culinaris | lentil |
| Linum usitatissimum | flax |
| Lycopersicon lycopersicum | tomato |
| Malus spp. | apple |
| Manihot esculenta | cassava |
| Medicago sativa | alfalfa |
| Musa spp. | bananas |
| Nicotiana tabacum (N. rustica) | tobacco |
| Olea europaea | olive |
| Oryza sativa | rice |
| Phaseolus lunatus | lima bean |
| Phaseolus vulgaris | bush bean |
| Picea abies | spruce |
| Pinus spp. | pines |
| Pisum sativum | garden pea |
| Prunus avium | sweet cherry |
| Prunus persica | peach |
| Pyrus communis | pear |
| Ribes sylvestre | redcurrant |
| Ribes uva crispa | gooseberry |
| Ricinus communis | castor oil |
| Saccharum officinarum | sugar cane |
| Secale cereale | rye |
| Solanum tuberosum | potato |
| Sorghum bicolor (S. vulgare) | sorghum |
| Theobroma cacao | cocoa |
| Trifolium pratense | red clover |
| Triticum aestivum | wheat |
| Triticum durum | durum wheat |
| Vicia faba | horse bean |
| Vitis vinifera | grapevine |
| Zea mays | corn |

To extend the spectrum of action and to achieve synergistic effects, the triazinyl-substituted sulfonylureas of the formula I can be mixed and applied together with many representatives of other groups of herbicides or growth regulators. Examples of suitable mixing partners are diazines, 4H-3,1-benzoxazine derivatives, benzothiadiazinones, 2,6-dinitroanilines, N-phenylcarbamates, thiocarbamates halo carboxylic acids, triazines, amides, ureas, diphenyl ethers, triazinones, uracils, benzofuran derivatives, cyclohexane-1,3-dione derivatives, quinolinecarboxylic acid derivatives, sulfonylureas, phenyloxy- and hetaryloxy-phenoxypropionic acids and the salts, esters and amides thereof, inter alia.

It may also be beneficial to apply the compounds of the formula I, alone or combined with other herbicides, also mixed together with other crop protection agents, for example with agents for controlling pests or phytopathogenic fungi or bacteria. Also of interest is the miscibility with mineral salt solutions which are employed to eliminate deficiencies of nutrients and trace elements. It is also possible to add non-phytotoxic oils and oil concentrates.

Examples of the synthesis of compounds I follow.

EXAMPLE 1 i-Propyl 2-[3-(4-methoxy-6-trifluoromethyl-1,3, 5-triazin-2-yl)ureidosulfonyl]benzoate A solution of 5.4 g of 2-(i-propoxycarbonyl) benzenesulfonyl isocyanate (20 mmol) in 5.4 g of 1,2-dichloroethane is added dropwise over the course of 5 min to a solution of 3.9 g of 2-amino-4-methoxy-6-trifluoromethyl-1,3, 5-triazine (20 mmol) in 150 ml of 1,2-dichloroethane at 25° C. The mixture is stirred at 25° C. for 16 h and then at 50° C. for 2 h. After removal of the volatiles under waterpump vacuum at 60° C., the residue is stirred with a mixture of ethanol and pentane, when crystallization occurs. The product is filtered off with suction and dried at 50° C. under waterpump vacuum. 6.1 g of the title compound (13 mmol; 66% of theory) are isolated with melting point 182°–185° C.

EXAMPLE 2

Calcium salt of i-propyl 2-[3-(4-methoxy-6-trifluoromethyl-1,3, 5-triazin-2-yl)ureidosulfonyl]benzoate 67 mg of $CaH_2$ (1.6 mmol) are introduced into 50 ml of methanol and stirred at 50° C. for 1 hour. 1.5 g of i-propyl 2-[3-(4-methoxy-6-trifluoromethyl-1,3, 5-triazin-2-yl)ureidosulfonyl]benzoate (3.2 mmol) are added and then the mixture is stirred at 25° C. for 1 h, resulting in a homogeneous solution. Removal of the volatiles under waterpump vacuum at 80° C. results in the title compound in quantitative yield with a decomposition point of 160° C.

EXAMPLE 3 i-Propyl 4-chloro-2-[3-(4-methoxy-6-trifluoromethyl-1,3,5-triazin-2-yl)ureidosulfonyl]benzoate 19.6 g of a solution of 6.1 g of 5-chloro-2-(i-propoxycarbonyl)benzenesulfonyl isocyanate (20 mmol) in 1,2-dichloroethane are added dropwise to a solution of 3.9 g of 2-amino-4-methoxy-6-trifluoromethyl-1, 3,5-triazine (20 mmol) in 150 ml of 1,2-dichloroethane at 25° C. The mixture is stirred at 25° C. for 16 h and then at 50° C. for 3 h. After removal of volatiles under waterpump vacuum at 60° C., the residue is extracted with 200 ml of a mixture of tert-butyl methyl ether and diethyl ether. The solvents are removed under waterpump vacuum at 50° C. and the residue is stirred in a little i-propanol. The solid product is filtered off with suction and dried under waterpump vacuum at 40° C. This results in 7.2 g of the title compound (14 mmol; 70% of theory) of melting point 160°–163° C.

EXAMPLE 4

Sodium salt of i-propyl 4-chloro-2-[3-(4-methoxy-6-trifluoromethyl-1,3,5-triazin-2-yl) ureidosulfonyl]benzoate 0.7 g of a sodium methanolate solution (30% by weight in methanol, 3.9 mmol) is added dropwise at 25° C. to a solution of 1.9 g of i-propyl 4-chloro-2-[3 -(4-methoxy-6-trifluoromethyl-1,3,5-triazin-2 -yl)ureidosulfonyl]benzoate (3.8 mmol) in 30 ml of methanol, the mixture is stirred at 25° C. for 10 min and the volatiles are removed under waterpump vacuum at 60° C. This results in the title compound in quantitative yield with a decomposition point of 175° C.

The active ingredients specified in Table 1 which follows are prepared in a similar way.

TABLE 1

| No. | $R^1$ | $R^2$ | $R^3$ | m.p. [°C.] |
|---|---|---|---|---|
| 1.01 | $CH_3$ | $i-C_3H_7$ | H | 182–185 |
| 1.02 | $CH_3$ | $i-C_3H_7$ | 4-Cl | 160–163 |
| 1.03 | $CH_3$ | $i-C_3H_7$ | H | 160 (decomp.), Ca salt |
| 1.04 | $CH_3$ | $i-C_3H_7$ | 4-Cl | 175 (decomp.), Ca salt |
| 1.05 | $CH_3$ | $CH_2CH_2Cl$ | H | 171–173 |
| 1.06 | $CH_3$ | $CH_2CH_2Cl$ | H | 162 (decomp.), Na salt |
| 1.07 | $CH_3$ | $CH_2CH_2OCH_3$ | H | 135–138 |
| 1.08 | $CH_3$ | $CH_2CH_2OCH_3$ | H | 145 (decomp.), Na salt |
| 1.09 | $CH_3$ | $n-C_3H_7$ | H | 175–176 |

The compounds listed in Table 2 can be prepared in a corresponding manner.

TABLE 2 with $R^1 = CH_3$ or $C_2H_5$

| $R^2$ | $R^3$ | |
|---|---|---|
| $n-C_3H_7$ | H | Na-salt |
| $n-C_3H_7$ | H | Ca-salt |
| $n-C_3H_7$ | 3-F | |
| $n-C_3H_7$ | 3-F | Na-salt |
| $n-C_3H_7$ | 3-F | Ca-salt |
| $n-C_3H_7$ | 4-F | |
| $n-C_3H_7$ | 4-F | Na-salt |
| $n-C_3H_7$ | 4-F | Ca-salt |
| $n-C_3H_7$ | 5-F | |
| $n-C_3H_7$ | 5-F | Na-salt |
| $n-C_3H_7$ | 5-F | Ca-salt |
| $n-C_3H_7$ | 6-F | |
| $n-C_3H_7$ | 6-F | Na-salt |
| $n-C_3H_7$ | 6-F | Ca-salt |
| $n-C_3H_7$ | 3-Cl | |
| $n-C_3H_7$ | 3-Cl | Na-salt |
| $n-C_3H_7$ | 3-Cl | Ca-salt |
| $n-C_3H_7$ | 4-Cl | |
| $n-C_3H_7$ | 4-Cl | Na-salt |
| $n-C_3H_7$ | 4-Cl | Ca-salt |
| $n-C_3H_7$ | 5-Cl | |
| $n-C_3H_7$ | 5-Cl | Na-salt |
| $n-C_3H_7$ | 5-Cl | Ca-salt |
| $n-C_3H_7$ | 6-Cl | |
| $n-C_3H_7$ | 6-Cl | Na-salt |
| $n-C_3H_7$ | 6-Cl | Ca-salt |
| $i-C_3H_7$ | H | Na— |
| $i-C_3H_7$ | H | Ca-salt |
| $i-C_3H_7$ | 3-F | |
| $i-C_3H_7$ | 3-F | Na-salt |
| $i-C_3H_7$ | 3-F | Ca-salt |
| $i-C_3H_7$ | 4-F | |
| $i-C_3H_7$ | 4-F | Na-salt |
| $i-C_3H_7$ | 4-F | Ca-salt |
| $i-C_3H_7$ | 5-F | |

TABLE 2-continued

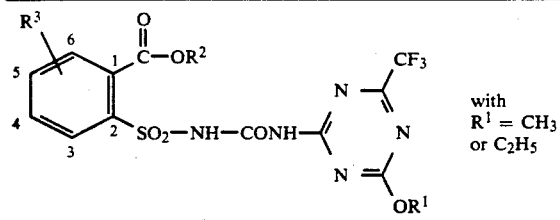
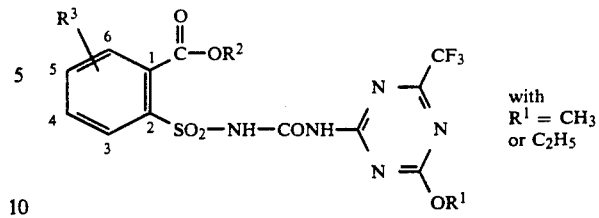

with $R^1 = CH_3$ or $C_2H_5$

| R² | R³ | |
|---|---|---|
| i-C₃H₇ | 5-F | Na-salt |
| i-C₃H₇ | 5-F | Ca-salt |
| i-C₃H₇ | 6-F | |
| i-C₃H₇ | 6-F | Na-salt |
| i-C₃H₇ | 6-F | Ca-salt |
| i-C₃H₇ | 3-Cl | |
| i-C₃H₇ | 3-Cl | Na-salt |
| i-C₃H₇ | 3-Cl | Ca-salt |
| i-C₃H₇ | 4-Cl | Na-salt |
| CH₂CH₂Cl | 5-Cl | |
| CH₂CH₂Cl | 5-Cl | Na-salt |
| CH₂CH₂Cl | 5-Cl | Ca-salt |
| CH₂CH₂Cl | 6-Cl | |
| CH₂CH₂Cl | 6-Cl | Na-salt |
| CH₂CH₂Cl | 6-Cl | Ca-salt |
| CH₂CH₂OCH₃ | H | Ca-salt |
| CH₂CH₂OCH₃ | 3-F | |
| CH₂CH₂OCH₃ | 3-F | Na-salt |
| CH₂CH₂OCH₃ | 3-F | Ca-salt |
| CH₂CH₂OCH₃ | 4-F | |
| CH₂CH₂OCH₃ | 4-F | Na-salt |
| CH₂CH₂OCH₃ | 4-F | Ca-salt |
| CH₂CH₂OCH₃ | 5-F | |
| CH₂CH₂OCH₃ | 5-F | Na-salt |
| CH₂CH₂OCH₃ | 5-F | Ca-salt |
| CH₂CH₂OCH₃ | 6-F | |
| CH₂CH₂OCH₃ | 6-F | Na-salt |
| CH₂CH₂OCH₃ | 6-F | Ca-salt |
| CH₂CH₂OCH₃ | 3-Cl | |
| CH₂CH₂OCH₃ | 3-Cl | Na-salt |
| CH₂CH₂OCH₃ | 3-Cl | Ca-salt |
| CH₂CH₂OCH₃ | 4-Cl | |
| CH₂CH₂OCH₃ | 4-Cl | Na-salt |
| CH₂CH₂OCH₃ | 4-Cl | Ca-salt |
| CH₂CH₂F | 5-Cl | |
| CH₂CH₂F | 5-Cl | Na-salt |
| CH₂CH₂F | 5-Cl | Ca-salt |
| CH₂CH₂F | 6-Cl | |
| CH₂CH₂F | 6-Cl | Na-salt |
| CH₂CH₂F | 6-Cl | Ca-salt |
| CH₂CH₂Cl | H | Ca-salt |
| CH₂CH₂Cl | 3-F | |
| CH₂CH₂Cl | 3-F | Na-salt |
| CH₂CH₂Cl | 3-F | Ca-salt |
| CH₂CH₂Cl | 4-F | |
| CH₂CH₂Cl | 4-F | Na-salt |
| CH₂CH₂Cl | 4-F | Ca-salt |
| CH₂CH₂Cl | 5-F | |
| CH₂CH₂Cl | 5-F | Na-salt |
| CH₂CH₂Cl | 5-F | Ca-salt |
| CH₂CH₂Cl | 6-F | |
| CH₂CH₂Cl | 6-F | Na-salt |
| CH₂CH₂Cl | 6-F | Ca-salt |
| CH₂CH₂Cl | 3-Cl | |
| CH₂CH₂Cl | 3-Cl | Na-salt |
| CH₂CH₂Cl | 3-Cl | Ca-salt |
| CH₂CH₂Cl | 4-Cl | |
| CH₂CH₂Cl | 4-Cl | Na-salt |
| CH₂CH₂Cl | 4-Cl | Ca-salt |
| i-C₃H₇ | 5-Cl | |
| i-C₃H₇ | 5-Cl | Na-salt |
| i-C₃H₇ | 5-Cl | Ca-salt |
| i-C₃H₇ | 6-Cl | |
| i-C₃H₇ | 6-Cl | Na-salt |
| i-C₃H₇ | 6-Cl | Ca-salt |
| CH₂CH₂F | H | |
| CH₂CH₂F | H | Na-salt |
| CH₂CH₂F | H | Ca-salt |
| CH₂CH₂F | 3-F | |
| CH₂CH₂F | 3-F | Na-salt |
| CH₂CH₂F | 3-F | Ca-salt |
| CH₂CH₂F | 4-F | |
| CH₂CH₂F | 4-F | Na-salt |
| CH₂CH₂F | 4-F | Ca-salt |
| CH₂CH₂F | 5-F | |
| CH₂CH₂F | 5-F | Na-salt |
| CH₂CH₂F | 5-F | Ca-salt |
| CH₂CH₂F | 6-F | |
| CH₂CH₂F | 6-F | Na-salt |
| CH₂CH₂F | 6-F | Ca-salt |
| CH₂CH₂F | 3-Cl | |
| CH₂CH₂F | 3-Cl | Na-salt |
| CH₂CH₂F | 3-Cl | Ca-salt |
| CH₂CH₂F | 4-Cl | |
| CH₂CH₂F | 4-Cl | Na-salt |
| CH₂CH₂F | 4-Cl | Ca-salt |
| CH₂CH₂OCH₃ | 5-Cl | |
| CH₂CH₂OCH₃ | 5-Cl | Na-salt |
| CH₂CH₂OCH₃ | 5-Cl | Ca-salt |
| CH₂CH₂OCH₃ | 6-Cl | |
| CH₂CH₂OCH₃ | 6-Cl | Na-salt |
| CH₂CH₂OCH₃ | 6-Cl | Ca-salt |
| CH₃ | 3-CH₃ | |
| CH₃ | 3-CH₃ | Na-salt |
| CH₃ | 3-CH₃ | Ca-salt |
| CH₃ | 4-CH₃ | |
| CH₃ | 4-CH₃ | Na-salt |
| CH₃ | 4-CH₃ | Ca-salt |
| CH₃ | 5-CH₃ | |
| CH₃ | 5-CH₃ | Na-salt |
| CH₃ | 5-CH₃ | Ca-salt |
| CH₃ | 6-CH₃ | |
| CH₃ | 6-CH₃ | Na-salt |
| CH₃ | 6-CH₃ | Ca-salt |
| C₂H₅ | 3-CH₃ | |
| C₂H₅ | 3-CH₃ | Na-salt |
| C₂H₅ | 3-CH₃ | Ca-salt |
| C₂H₅ | 4-CH₃ | |
| C₂H₅ | 4-CH₃ | Na-salt |
| C₂H₅ | 4-CH₃ | Ca-salt |
| C₂H₅ | 5-CH₃ | |
| C₂H₅ | 5-CH₃ | Na-salt |
| C₂H₅ | 5-CH₃ | Ca-salt |
| C₂H₅ | 6-CH₃ | |
| C₂H₅ | 6-CH₃ | Na-salt |
| C₂H₅ | 6-CH₃ | Ca-salt |
| n-C₃H₇ | 3-CH₃ | |
| n-C₃H₇ | 3-CH₃ | Na-salt |
| n-C₃H₇ | 3-CH₃ | Ca-salt |
| n-C₃H₇ | 4-CH₃ | |
| n-C₃H₇ | 4-CH₃ | Na-salt |
| n-C₃H₇ | 4-CH₃ | Ca-salt |
| n-C₃H₇ | 5-CH₃ | |
| n-C₃H₇ | 5-CH₃ | Na-salt |
| n-C₃H₇ | 5-CH₃ | Ca-salt |
| n-C₃H₇ | 6-CH₃ | |
| n-C₃H₇ | 6-CH₃ | Na-salt |
| n-C₃H₇ | 6-CH₃ | Ca-salt |
| i-C₃H₇ | 3-CH₃ | |
| i-C₃H₇ | 3-CH₃ | Na-salt |
| i-C₃H₇ | 3-CH₃ | Ca-salt |
| i-C₃H₇ | 4-CH₃ | |
| i-C₃H₇ | 4-CH₃ | Na-salt |
| i-C₃H₇ | 4-CH₃ | Ca-salt |
| i-C₃H₇ | 5-CH₃ | |
| i-C₃H₇ | 5-CH₃ | Na-salt |
| i-C₃H₇ | 5-CH₃ | Ca-salt |
| i-C₃H₇ | 6-CH₃ | |
| i-C₃H₇ | 6-CH₃ | Na-salt |
| i-C₃H₇ | 6-CH₃ | Ca-salt |

TABLE 2-continued

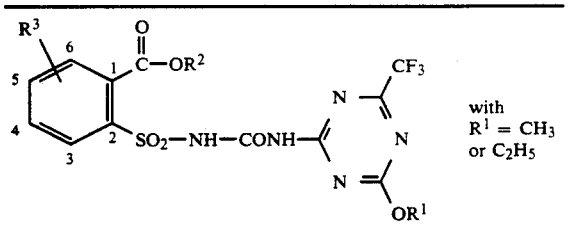

with $R^1 = CH_3$ or $C_2H_5$

| $R^2$ | $R^3$ | |
|---|---|---|
| $CH_2CH_2F$ | 3-$CH_3$ | |
| $CH_2CH_2F$ | 3-$CH_3$ | Na-salt |
| $CH_2CH_2F$ | 3-$CH_3$ | Ca-salt |
| $CH_2CH_2F$ | 4-$CH_3$ | |
| $CH_2CH_2F$ | 4-$CH_3$ | Na-salt |
| $CH_2CH_2F$ | 4-$CH_3$ | Ca-salt |
| $CH_2CH_2F$ | 5-$CH_3$ | |
| $CH_2CH_2F$ | 5-$CH_3$ | Na-salt |
| $CH_2CH_2F$ | 5-$CH_3$ | Ca-salt |
| $CH_2CH_2F$ | 6-$CH_3$ | |
| $CH_2CH_2F$ | 6-$CH_3$ | Na-salt |
| $CH_2CH_2F$ | 6-$CH_3$ | Ca-salt |
| $CH_2CH_2F$ | 3-$CH_3$ | |
| $CH_2CH_2F$ | 3-$CH_3$ | Na-salt |
| $CH_2CH_2F$ | 3-$CH_3$ | Ca-salt |
| $CH_2CH_2Cl$ | 4-$CH_3$ | |
| $CH_2CH_2Cl$ | 4-$CH_3$ | Na-salt |
| $CH_2CH_2Cl$ | 4-$CH_3$ | Ca-salt |
| $CH_2CH_2Cl$ | 5-$CH_3$ | |
| $CH_2CH_2Cl$ | 5-$CH_3$ | Na-salt |
| $CH_2CH_2Cl$ | 5-$CH_3$ | Ca-salt |
| $CH_2CH_2Cl$ | 6-$CH_3$ | |
| $CH_2CH_2Cl$ | 6-$CH_3$ | Na-salt |
| $CH_2CH_2Cl$ | 6-$CH_3$ | Ca-salt |
| $CH_2CH_2OCH_3$ | 3-$CH_3$ | |
| $CH_2CH_2OCH_3$ | 3-$CH_3$ | Na-salt |
| $CH_2CH_2OCH_3$ | 3-$CH_3$ | Ca-salt |
| $CH_2CH_2OCH_3$ | 4-$CH_3$ | |
| $CH_2CH_2OCH_3$ | 4-$CH_3$ | Na-salt |
| $CH_2CH_2OCH_3$ | 4-$CH_3$ | Ca-salt |
| $CH_2CH_2OCH_3$ | 5-$CH_3$ | |
| $CH_2CH_2OCH_3$ | 5-$CH_3$ | Na-salt |
| $CH_2CH_2OCH_3$ | 5-$CH_3$ | Ca-salt |
| $CH_2CH_2OCH_3$ | 6-$CH_3$ | |
| $CH_2CH_2OCH_3$ | 6-$CH_3$ | Na-salt |
| $CH_2CH_2OCH_3$ | 6-$CH_3$ | Ca-salt |
| $CH_3$ | 3-$OCH_3$ | |
| $CH_3$ | 3-$OCH_3$ | Na-salt |
| $CH_3$ | 3-$OCH_3$ | Ca-salt |
| $CH_3$ | 4-$OCH_3$ | |
| $CH_3$ | 4-$OCH_3$ | Na-salt |
| $CH_3$ | 4-$OCH_3$ | Ca-salt |
| $CH_3$ | 5-$OCH_3$ | |
| $CH_3$ | 5-$OCH_3$ | Na-salt |
| $CH_3$ | 5-$OCH_3$ | Ca-salt |
| $CH_3$ | 6-$OCH_3$ | |
| $CH_3$ | 6-$OCH_3$ | Na-salt |
| $CH_3$ | 6-$OCH_3$ | Ca-salt |
| $C_2H_5$ | 3-$OCH_3$ | |
| $C_2H_5$ | 3-$OCH_3$ | Na-salt |
| $C_2H_5$ | 3-$OCH_3$ | Ca-salt |
| $C_2H_5$ | 4-$OCH_3$ | |
| $C_2H_5$ | 4-$OCH_3$ | Na-salt |
| $C_2H_5$ | 4-$OCH_3$ | Ca-salt |
| $C_2H_5$ | 5-$OCH_3$ | |
| $C_2H_5$ | 5-$OCH_3$ | Na-salt |
| $C_2H_5$ | 5-$OCH_3$ | Ca-salt |
| $C_2H_5$ | 6-$OCH_3$ | |
| $C_2H_5$ | 6-$OCH_3$ | Na-salt |
| $C_2H_5$ | 6-$OCH_3$ | Ca-salt |
| n-$C_3H_7$ | 3-$OCH_3$ | |
| n-$C_3H_7$ | 3-$OCH_3$ | Na-salt |
| n-$C_3H_7$ | 3-$OCH_3$ | Ca-salt |
| n-$C_3H_7$ | 4-$OCH_3$ | |
| n-$C_3H_7$ | 4-$OCH_3$ | Na-salt |
| n-$C_3H_7$ | 4-$OCH_3$ | Ca-salt |
| n-$C_3H_7$ | 5-$OCH_3$ | |
| n-$C_3H_7$ | 5-$OCH_3$ | Na-salt |
| n-$C_3H_7$ | 5-$OCH_3$ | Ca-salt |
| n-$C_3H_7$ | 6-$OCH_3$ | |

TABLE 2-continued

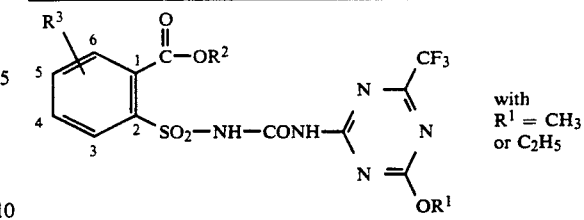

with $R^1 = CH_3$ or $C_2H_5$

| $R^2$ | $R^3$ | |
|---|---|---|
| n-$C_3H_7$ | 6-$OCH_3$ | Na-salt |
| n-$C_3H_7$ | 6-$OCH_3$ | Ca-salt |
| i-$C_3H_7$ | 3-$OCH_3$ | |
| i-$C_3H_7$ | 3-$OCH_3$ | Na-salt |
| i-$C_3H_7$ | 3-$OCH_3$ | Ca-salt |
| i-$C_3H_7$ | 4-$OCH_3$ | |
| i-$C_3H_7$ | 4-$OCH_3$ | Na-salt |
| i-$C_3H_7$ | 4-$OCH_3$ | Ca-salt |
| i-$C_3H_7$ | 5-$OCH_3$ | |
| i-$C_3H_7$ | 5-$OCH_3$ | Na-salt |
| i-$C_3H_7$ | 5-$OCH_3$ | Ca-salt |
| i-$C_3H_7$ | 6-$OCH_3$ | |
| i-$C_3H_7$ | 6-$OCH_3$ | Na-salt |
| i-$C_3H_7$ | 6-$OCH_3$ | Ca-salt |
| $CH_2CH_2F$ | 3-$OCH_3$ | |
| $CH_2CH_2F$ | 3-$OCH_3$ | Na-salt |
| $CH_2CH_2F$ | 3-$OCH_3$ | Ca-salt |
| $CH_2CH_2F$ | 4-$OCH_3$ | |
| $CH_2CH_2F$ | 4-$OCH_3$ | Na-salt |
| $CH_2CH_2F$ | 4-$OCH_3$ | Ca-salt |
| $CH_2CH_2F$ | 5-$OCH_3$ | |
| $CH_2CH_2F$ | 5-$OCH_3$ | Na-salt |
| $CH_2CH_2F$ | 5-$OCH_3$ | Ca-salt |
| $CH_2CH_2F$ | 6-$OCH_3$ | |
| $CH_2CH_2F$ | 6-$OCH_3$ | Na-salt |
| $CH_2CH_2F$ | 6-$OCH_3$ | Ca-salt |
| $CH_2CH_2Cl$ | 3-$OCH_3$ | |
| $CH_2CH_2Cl$ | 3-$OCH_3$ | Na-salt |
| $CH_2CH_2Cl$ | 3-$OCH_3$ | Ca-salt |
| $CH_2CH_2Cl$ | 4-$OCH_3$ | |
| $CH_2CH_2Cl$ | 4-$OCH_3$ | Na-salt |
| $CH_2CH_2Cl$ | 4-$OCH_3$ | Ca-salt |
| $CH_2CH_2Cl$ | 5-$OCH_3$ | |
| $CH_2CH_2Cl$ | 5-$OCH_3$ | Na-salt |
| $CH_2CH_2Cl$ | 5-$OCH_3$ | Ca-salt |
| $CH_2CH_2Cl$ | 6-$OCH_3$ | |
| $CH_2CH_2Cl$ | 6-$OCH_3$ | Na-salt |
| $CH_2CH_2Cl$ | 6-$OCH_3$ | Ca-salt |
| $CH_2CH_2OCH_3$ | 3-$OCH_3$ | |
| $CH_2CH_2OCH_3$ | 3-$OCH_3$ | Na-salt |
| $CH_2CH_2OCH_3$ | 3-$OCH_3$ | Ca-salt |
| $CH_2CH_2OCH_3$ | 4-$OCH_3$ | |
| $CH_2CH_2OCH_3$ | 4-$OCH_3$ | Na-salt |
| $CH_2CH_2OCH_3$ | 4-$OCH_3$ | Ca-salt |
| $CH_2CH_2OCH_3$ | 5-$OCH_3$ | |
| $CH_2CH_2OCH_3$ | 5-$OCH_3$ | Na-salt |
| $CH_2CH_2OCH_3$ | 5-$OCH_3$ | Ca-salt |
| $CH_2CH_2OCH_3$ | 6-$OCH_3$ | |
| $CH_2CH_2OCH_3$ | 6-$OCH_3$ | Na-salt |
| $CH_2CH_2OCH_3$ | 6-$OCH_3$ | Ca-salt |

EXAMPLES OF USE

The herbicidal action of the 1,3, 5-triazin-2-ylureidosulfonylbenzoic esters of the formula I on the growth of the test plants is shown by the following glass house tests.

The plants are grown in plastic flowerpots with a capacity of 300 cm³ containing loamy sand with about 3% humus as substrate. The seeds of the test plants are sown shallowly, keeping the species separate.

For post-emergence treatment, either plants which have been directly sown or have grown in the same vessels are selected or they are grown separately and transplanted into the test vessels a few days before the treatment.

Depending on species, these plants are treated at a height of from 3 to 15 cm with the active ingredients which have been suspended or emulsified in water as dispersant and are sprayed using finely dispersing nozzles. The application rate for post-emergence treatment is 0.06 kg/ha active substance.

The test vessels are placed in a glass house at from 20° to 35° C. for thermophilic species and at from 10° to 20° C. for those preferring a more temperate climate. The tests last from 2 to 4 weeks. During this period the plants are tended and their reaction to the individual treatment is evaluated.

A scale from 0 to 100 is used for assessment, 100 meaning no emergence of the plants or complete destruction of at least the above-ground parts and 0 meaning no damage or normal growth.

The plants used in the glass house tests comprise the following species:

| Latin name | English name | Abbreviation |
|---|---|---|
| Amaranthus retroflexus | pigweed | AMARE |
| Cyperus iria | — | CYPIR |
| Galium aparine | catchweed | GALAP |
| Ipomoea spp. | morning glory | IPOSS |
| Polygonum persicaria | redshanks | POLPE |
| Triticum aestivum | soft wheat | TRZAS |
| Veronica spp. | speedwell species | VERSS |

Unwanted broad-leaved plants are controlled very well with 0.06 kg/ha active substance of Example 1 in the post-emergence method, while the selectivity is excellent with wheat as crop plant.

Table 3 which follows gives the results of biological investigations comparing novel active ingredient No. 1 with the comparison compound A disclosed in EP-A 7687.

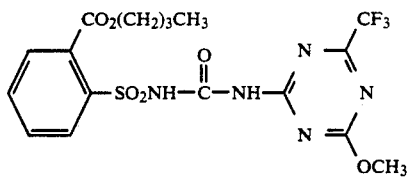

TABLE 3

Comparison of the novel compound and comparison agent A on post-emergence treatment with 0.06 kg/ha active substance in a glass house

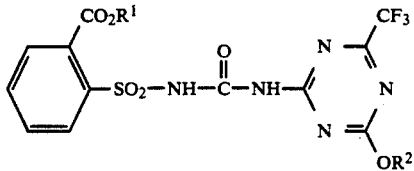

| Exp. No. | $R^1$ | $R^2$ | Test plants and damage [%] | | | | | | |
|---|---|---|---|---|---|---|---|---|---|
| | | | TRZAS | CYPIR | AMARE | GALAP | IPOSS | POLPE | VERSS |
| 1 | i-$C_3H_7$ | $CH_3$ | 20 | 80 | 80 | 75 | 60 | 30 | 85 |
| A | n-$C_4H_9$ | $CH_3$ | 0 | 0 | 0 | 0 | 10 | 0 | 0 |

We claim:

1. A 1,3,5-triazin-2-ylureidosulfonylbenzoic ester of the formula I where
$R^1$ is methyl or ethyl;
$R^2$ is n-propyl, i-propyl, 2-haloethyl or 2-methoxyethyl and, when $R^3$ is methyl or methoxy, is methyl or ethyl;
$R^3$ is hydrogen, fluorine, chlorine, methyl or methoxy, or its salts thereof which can be used in agriculture.

2. A herbicidal composition comprising a herbicidally effective amount of a 1,3,5-triazin-2-ylureidosulfonylbenzoic ester of the formula I as defined in claim 1 or its salt and carriers conventional for this purpose.

3. A method for controlling unwanted plant growth, which comprises exposing the plants and/or their habitat to a herbicidally effective amount of a 1,3, 5-triazin-2-ylureidosulfonylbenzoic ester of the formula I as defined in claim 1 or one of its salts.

4. A compound of claim 1, wherein $R^2$ is methyl or ethyl and $R^3$ is methyl or methoxy.

5. A compound of claim 1, wherein $R^2$ is n-propyl, i-propyl, 2-haloethyl or 2-methoxyethyl.

6. A compound of the formula I wherein $R^1$ is methyl or ethyl; $R^2$ is methyl, ethyl, n-propyl, i-propyl, 2-haloethyl or 2-methoxyethyl; and $R^3$ is methoxy; or an alkali metal or alkaline earth metal salt thereof.

7. A herbicidal composition comprising a herbicidally effective amount of a compound of claim 6 and an inert carrier therefor.

8. A method for controlling unwanted plant growth, comprising applying a herbicidally effective amount of a compound according to claim 6 to the said unwanted plants and/or their habitat.

* * * * *